United States Patent [19]

Nohara et al.

[11] Patent Number: 4,539,326

[45] Date of Patent: Sep. 3, 1985

[54] 5-OXO-5H-(1)BENZOPYRANO(2,3-b)PYRIDINE DERIVATIVES, THEIR PRODUCTION AND USE AS ANTI-INFLAMMATORY AGENTS

[75] Inventors: Akira Nohara, Kyoto; Seiji Kuzuna, Kawanishi, both of Japan

[73] Assignee: Takeda Chemical Industries, Ltd., Osaka, Japan

[21] Appl. No.: 510,723

[22] Filed: Jul. 5, 1983

[30] Foreign Application Priority Data

Aug. 20, 1982 [JP] Japan ................................. 57-145274
May 19, 1983 [JP] Japan ................................. 58-88915

[51] Int. Cl.³ ................ C07D 491/00; C07D 221/18; C07D 471/00; A61K 31/435
[52] U.S. Cl. ...................................... 514/285; 514/291; 546/89; 546/77; 546/92; 546/62
[58] Field of Search ............... 546/80, 89, 77, 92, 546/62; 424/256

[56] References Cited

U.S. PATENT DOCUMENTS

| | | | |
|---|---|---|---|
| 3,931,199 | 1/1976 | Nakanishi et al. | 546/80 |
| 3,931,205 | 1/1976 | Nakanishi et al. | 546/80 |
| 4,143,042 | 3/1979 | Nohara et al. | 546/80 |
| 4,255,576 | 3/1981 | Nohara et al. | 546/80 |
| 4,299,963 | 11/1981 | Nohara et al. | 546/80 |
| 4,302,463 | 11/1981 | Ishiguro et al. | 546/80 |

OTHER PUBLICATIONS

Liebig Ann. Chem. 1976, 1659-1662.

*Primary Examiner*—Henry R. Jiles
*Assistant Examiner*—Robert C. Whittenbaugh
*Attorney, Agent, or Firm*—Wegner & Bretschneider

[57] ABSTRACT

The present invention relates to novel 5-oxo-5H-[1]benzopyrano[2,3-b]pyridine derivatives useful for effective medicines for the treatment of various connective tissue diseases such as chronic rheumatoid arthritis and varieties of inflammatory diseases caused by immunoreaction, which have the following formula:

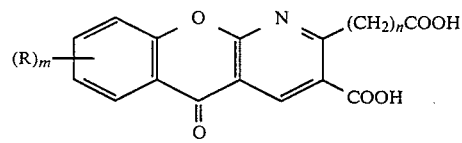

wherein R is the same or different and represents hydrogen, alkyl, alkoxy, nitro, hydroxyl, acyl, hydroxyalkyl, halogen with the proviso that m is 1,2 or 3, or a tetramethylene (—(CH$_2$)$_4$—) or butadienylene (—CH=CH—CH=CH—) group which, in conjunction with two adjacent carbon atoms on the ring, forms a six-membered ring with the proviso that m is 1; n is 1 or 2, or a physiologically acceptable salt or ester thereof.

27 Claims, No Drawings

5-OXO-5H-(1)BENZOPYRANO(2,3-b)PYRIDINE DERIVATIVES, THEIR PRODUCTION AND USE AS ANTI-INFLAMMATORY AGENTS

The present invention relates to 5-oxo-5H-[1]benzopyrano[2,3-b]pyridine derivatives of the formula [I]:

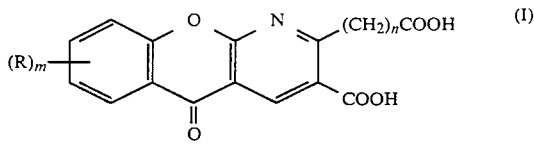

wherein R is the same or different and represents hydrogen, alkyl, alkoxy, nitro, hydroxy, acyl, hydroxyalkyl or halogen with the proviso that m is 1,2 or 3, or a tetramethylene ($-(CH_2)_4-$) or butadienylnene ($-CH=CH-CH=CH-$) group which, in conjunction with two adjacent carbon atoms on the ring, forms a six-membered ring with the proviso that m is 1; n is 1 or 2, or physiologically acceptable salts or esters thereof, to a process for producing the same and to pharmaceutical compositions containing the same.

The compounds of the formula (I) according to the present invention, or physiologically acceptable salts or esters thereof, can be produced by reacting a 4-oxo-4H-1-benzopyran-3-carbonitrile of the formula (II):

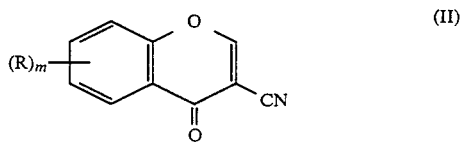

wherein R and m have the same meaning as defined above, with a compound of the formula (III):

wherein $R_1$ is alkyl; n is 1 or 2, followed by subjecting the resultant reaction product to a hydrolysis reaction, if necessary.

The compounds of the formula (I) according to the present invention as obtained by the above procedure are of value as agents for the treatment of various connective tissue diseases such as chronic rheumatoid arthritis and varieties of inflammatory diseases caused by the immunoreaction.

With reference to the substituents R and $R_1$ in the above formulae, examples of alkyl represented by R include straight-chain or branched alkyl of 1 to 6 carbon atoms such as methyl, ethyl, propyl, isopropyl, butyl, t-butyl, pentyl and hexyl groups; also, examples of alkoxy include alkoxy having the alkyl moiety of 1 to 4 carbon atoms such as methoxy, ethoxy, propoxy and butoxy groups; as examples of acyl, there may be mentioned acyl of 2 to 4 carbon atoms such as acetyl, propionyl and butyryl groups, and examples of hydroxyalkyl include those of 1 to 4 carbon atoms such as hydroxymethyl, 1-hydroxyethyl, 1-hydroxypropyl, 1-hydroxy-1-methyl-ethyl and 1-hydroxybutyl, while as the halogen atom, there may be mentioned chlorine, bromine, iodine and fluorine. Among them, for practical purposes, alkyl, halogen and hydroxyalkyl are preferred, and alkyl of 1 to 3 carbon atoms, chlorine and hydroxyalkyl of 1 to 3 carbon atoms are more preferable. Examples of alkyl represented by $R_1$ in the formula (III) include alkyl of 1 to 4 carbon atoms such as methyl, ethyl, propyl, isopropyl, butyl and t-butyl.

As the salts of the compounds of the formula (I), by way of example, there may be mentioned physiologically acceptable salts formed with alkali metals such as sodium and potassium.

In more particular, the compounds of the formula (I) according to the present invention are produced by the following procedure: a compound of the formula (II) is reacted with an active methylene compound of the formula (III) to produce the compound of the formula (I). Normally, the amount of the active methylene compound to be used in the reaction is practically in the range of 1 to 5 moles per mole of the starting compound of the formula (II).

It is normally desirable that the above reaction is conducted in the presence of a base, and examples of the base which is usable include organic amines, such as secondary amines exemplified by piperidine, pyrrolidine, morpholine, diethylamine, dipropylamine and dibutylamine, tertiary amines typified by 1,8-diazobicyclo[5,4,0]undec-7-ene and triethylamine, and heterocyclic bases exemplified by imidazole and 2-methylimidazole. The amount of these organic bases to be used is normally in the range of catalytic amounts to 5 moles per mole of the starting compound of the formula (II).

The reaction, normally, is desirably conducted in organic solvent, and examples of such solvent include alcohols such as methanol, ethanol, propanol and butanol, dimethylformamide, etc. The reaction temperature, reaction time and other reaction conditions are not particularly limited, although the reaction is generally allowed to proceed at temperatures in the neighborhood of room temperature to the boiling point of the solvent used for a period of time within the range of about 1 to 24 hours.

From the diester compounds of the formula (I) as obtained by the above procedure, the compounds of (I) where R is 1-hydroxyalkyl can be derived to yield their corresponding acyl form by the conventional oxidation methods such as the Jones oxidation in acetone.

The diester compounds of the formula (I) can be derived to the compounds of the formula (I) or their salts by hydrolysis, if necessary. As the conditions of hydrolysis, use is made of the conventional acid hydrolysis or alkali hydrolysis method. In the acid hydrolysis, for example, hydrolysis is conducted normally at temperatures in the vicinity of room temperature to 150° C. with the use of an excess of sulfuric acid, hydrochloric acid, phosphoric acid, etc., solely or in combination with organic acids such as formic acid and acetic acid or in conjunction with alcohols such as methanol, ethanol and propanol or ethers such as tetrahydrofuran and dioxane. According to the alkali hydrolysis method, hydrolysis is carried out normally at temperatures in the vicinity of room temperature to 150° C. by use of sodium hydroxide, potassium hydroxide, barium hydroxide, etc. in excess, solely or in conjunction with the above-mentioned alcohols or ethers as solvent. The reaction temperature varies with the type of compounds, and is normally in the range of 1 hour to several days. In addition, the objective compounds can be produced by the combination of the acid hydrolysis and alkali hydrolysis, if the occasion arises.

The compounds of the formula (I) as produced by the above procedure can be used as agents for the treatment of various connective tissue diseases such as chronic rheumatoid arthritis and varieties of inflammatory diseases caused by the immunoreaction.

By means of a conventional method, the compounds of the formula (I) can be mixed with pharmaceutically acceptable carriers in conjunction with adjuvants to employ as preparations for oral administration such as tablets, granules, powders and capsules, and also can be dissolved in distilled water to use as preparations for injection, as well. In the case of formulation into tablets, granules and powders, preferred pharmaceutical carriers include lactose, starch, dextrin, white refined sugar, crystalline cellulose, kaolin, calcium carbonate, talc, etc., while for preparation of injections, it is preferable to render the resulting solution isotonic with sodium chloride or potassium chloride.

The amount of the compounds (I) of the formula (I) in the drug compositions is normally 10 to 2000 mg as the daily dose in adults, preferably 50 to 500 mg, for oral preparations, and is normally 1 to 500 mg as the daily dose in adults, preferably 5 to 100 mg, for injections.

Acute toxicity

Male Jcl: ICR strain mice (5-week old) were administered orally a 4% suspension of disodium (7-ethyl-3-carboxylato-5-oxo-5H-[1]benzopyrano[2,3-b]pyridin-2-yl)acetate in gum arabic. As a result, there was no abnormality observed with the oral dose of 2,000 mg/kg.

Below described are the experiment example and examples of the present invention, which are not to be understood to restrict the present invention.

EXPERIMENT EXAMPLE 1

Action of inhibiting adjuvant arthritis

As experimental animal, male Sprague-Dawley rats (6-week old) were used.

Adjuvant arthritis was induced by suspending killed cells of mycobacteria (*M. butyricum* strain) in liquid paraffin and injecting the rats with the resultant suspension beneath the skin of the hind-paw. The suspension obtained by suspending 70 mg of the test specimen [disodium(7-ethyl-3-carboxylato-5-oxo-5H-[1]benzopyrano[2,3-b]pyridin-2-yl)acetate] in 7 ml of 4% gum arabic was administered orally to rats once a day at a rate of 0.5 ml per 100 g of body weight for the consecutive 14 days after the injection of adjuvant. The degrees or severities of the inflammations induced on the other hind paw not injected with adjuvant, front paws, tail and ears were graded 1 to 5, and the grades were summed up for each animal, with the highest mark in total for the four body spots being 20. In addition, effects exerted by the administration on the increase in body weight (difference between the body weights measured after 14 days and on the day of sensitization) and the weight of thymus were investigated, and were compared with those obtained with the control group. The results are as shown in Table 1. The test specimen was found not only to improve the systemic inflammation score and the restraint of the increase in body weight accompanied by it, but also to increase the weight of thymus.

TABLE 1

| No. of days after sensitization | Systemic inflammation score | | Weight of thymus (mg) | Increase in body weight (g) |
|---|---|---|---|---|
| | 12 | 14 | 14 | 14 |
| Control | 7.0 ± 0.9 | 8.8 ± 0.7 | 211.7 ± 21.5 | 42.2 ± 2.5 |
| 50 mg/kg | 3.7 ± 1.1* | 4.7 ± 1.6* | 375 ± 52.0* | 50.0 ± 3.1 |

Note:
*; $P < 0.05$

The test specimen was found neither to exhibit the antiinflammatory activity in the rat carrageenin-induced edema method and the analgesic activity in the mouse phenylquinone writhing method nor to exert any effect on the prostaglandin synthetase originating from the bovine seminal vesicle.

EXPERIMENT EXAMPLE 2

Action of inhibiting adjuvant arthritis

As experimental animal, male Sprague-Dawley rats (6-week old) were used.

Adjuvant arthritis was induced by suspending killed cells of mycobacteria (*M. butyricum* strain) in liquid paraffine and injecting the rats with the resultant suspension beneath the skin of hind-paw. The suspension obtained by suspending 70 mg of the test specimen [ethyl(7-ethyl-3-ethoxycarbonyl-5-oxo-5H-[1]benzopyrano[2,3-b]pyridin-2-yl)acetate] in 7 ml of 4% gum arabic was administered orally to rats once a day at a rate of 0.5 ml per 100 g of body weight for the consecutive 14 days after the injection of adjuvant. The degrees or severities of the inflammations induced on the other hind paw not injected with adjuvant, front paws, tail and ears were graded 1 to 5, and the grades were summed up for each animal, with the highest mark in total for the four body spots being 20. In addition, effects exerted by the administration on the increase in body weight (difference between the body weights measured after 14 days and on the day of sensitization) and the weight of thymus were investigated, and were compared with those obtained with the control group. The results are as shown in Table 2. The test specimen was found to improve the systemic inflammation score and the restraint of the increase in body weight accompanied by it, and to have a tendency to increase the weight of thymus.

TABLE 2

| No. of days after sensitization | Systemic inflammation score | | Weight of thymus, (mg) | Increase in body weight (g) |
|---|---|---|---|---|
| | 12 | 14 | 14 | 14 |
| Control | 6.7 ± 0.8 | 8.0 ± 0.5 | 286.5 ± 34.3 | 42.5 ± 3.2 |
| 50 mg/kg | 3.3 ± 0.7** | 4.0 ± 1.0** | 444.2 ± 69.9 | 43.3 ± 8.6 |

Note:
**; $P < 0.01$

EXAMPLE 1

A mixture of 6-ethyl-4-oxo-4H-1-benzopyran-3-carbonitrile (1.99 g), dimethyl 1,3-acetonedicarboxylate (2 g), methanol (20 ml) and piperidine (0.2 ml) was heated under reflux for 3 hours and concentrated. Ethanol was added to the residue, and yellow crystals were recovered by filtration. The crystals were chromatographed on a column of silica gel (50 g) by using hexane-chloroformethyl acetate (10:10:1) as eluent. Recrystallization from methanol produced 1.04 g of pale yellow needles of methyl(7-ethyl-3-methoxycarbonyl-5-oxo-5H-[1]benzopyrano[2,3-b]pyridin-2-yl)acetate. m.p. 142°–143° C.

By following the same procedure, different diester derivatives of (3-alkoxycarbonyl-5-oxo-5H-[1]benzopyrano[2,3-b]pyridin-2-yl)acetic acid were obtained.

| Starting Compound | General formula (I) (n = 1) | | |
|---|---|---|---|
| | R | diesters | m.p. (°C.) |
| 4-Oxo-4H—1-benzopyran-3-carbonitrile | H | $CH_3$ | 166–168 |
| 6-Chlor-4-oxo-4H—1-benzopyran-3-carbonitrile | 7-Cl | $CH_3$ | 192–193 |
| 6-Isopropyl-4-oxo-4H—1-benzopyran-3-carbonitrile | 7-CH(CH$_3$)(CH$_3$) | $CH_3$ | 135–136 |
| 6,8-Dimethyl-4-oxo-4H—1-benzopyran-3-carbonitrile | 7,9-$(CH_3)_2$ | $CH_3$ | 197–198 |
| 6-Nitro-4-oxo-4H—1-benzopyran-3-carbonitrile | 7-$NO_2$ | $C_2H_5$ | 147.5–148.5 |
| 6-(1-Hydroxyethyl)-4-oxo-4H—1-benzopyran-3-carbonitrile | 7-($CH_3CH$—)OH | $C_2H_5$ | 124–126 |
| 6-t-Butyl-4-oxo-4H—1-benzopyran-3-carbonitrile | 7-$C(CH_3)_3$ | $CH_3$ | 152–153 |
| 6-Methoxy-4-oxo-4H—1-benzopyran-3-carbonitrile | 7-$OCH_3$ | $CH_3$ | 175–176.5 |
| 6-Hydroxy-4-oxo-4H—1-benzopyran-3-carbonitrile | 7-OH | $CH_3$ | 234.5–235.5 |

By following a similar procedure, there were prepared methyl(3-methoxycarbonyl-5-oxo-5H-[1]naphtho[2′,1′-2,3]pyrano[6,5-b]pyridin-2-yl)acetate with the melting point of 240°–245° C. from 4-oxo-4H-naphtho[2,1-b]pyran-3-carbonitrile and methyl(3-methoxycarbonyl-11-n-propyl-7,8,9,10-tetrahydro-5-oxo-5H-naphtho[2′,3′-2,3]pyrano[6,5-b]pyridin-2-yl)acetate with the melting point of 156°–157° C. from 10-n-propyl-6,7,8,9-tetrahydro-4-oxo-4H-naphtho[2,3-b]pyran-3-carbonitrile, respectively.

EXAMPLE 2

A mixture of 6-ethyl-4-oxo-4H-1-benzopyran-3-carbonitrile (1.99 g), diethyl β-ketoadipate (2.0 g), ethanol (15 ml) and piperidine (0.3 ml) was heated under reflux for 1.5 hours. After the mixture was cooled, the crystals which separated out were recovered by filtration and suspended in ethanol, followed by heating under reflux. After the suspension was cooled, the crystals were recovered by filtration to give 1.93 g of colorless long needls of ethyl(3-ethoxycarbonyl-7-ethyl-5-oxo-5H-[1]benzopyrano[2,3-b]pyridin-2-yl)propionate. m.p. 168°–170° C.

By following a similar procedure, there were prepared ethyl(3-ethoxycarbonyl-5-oxo-5H-[1]benzopyrano[2,3-b]pyridin-2-yl)propionate with the melting point of 150° to 151° C. from 4-oxo-4H-1-benzopyran-3-carbonitrile and ethyl 3-(7-chlor-3-ethoxycarbonyl-5-oxo-5H-[1]benzopyrano[2,3-b]pyridin-2-yl)propionate with the melting point of 128° to 129° C. from 6-chlor-4-oxo-4H-1-benzopyran-3-carbonitrile.

EXAMPLE 3

A 4 ml portion of the Jones reagent (prepared from 6.0 g of anhydrous chromic acid, 3.6 ml of 97% sulfuric acid and 18 ml of water) was added over a 20-minute period to a solution of ethyl(3-ethoxycarbonyl-7-(1-hydroxyethyl)-5-oxo-5H-[1]benzopyrano[2,3-b]pyridin-2-yl)acetate (3.99 g) in acetone (50 ml). After water (150 ml) was added to the reaction mixture, the crystals which separated out were recovered by filtration and dissolved in a mixture of chloroform:acetone:formic acid (80:1:0.1). The solution was chromatographed on a column of silica gel (140 g) to conduct the purification. Recrystallization from ethyl acetate yielded 3.14 g of colorless needles of ethyl(7-acetyl-3-ethoxycarbonyl-5-oxo-5H-[1]benzopyrano[2,3-b]pyridin-2-yl)acetate. m.p. 160°–161° C.

EXAMPLE 4

1N Aqueous sodium hydroxide solution (42 ml) was added to a solution of methyl(7-ethyl-3-methoxycarbonyl-5-oxo-5H-[1]benzopyrano[2,3-b]pyridin-2-yl)acetate (7.10 g) in tetrahydrofuran (100 ml), and the mixture was stirred at room temperature for 2 hours. After cooling, methanol (200 ml) was added to the reaction solution, and the crystals which separated out were recovered by filtration. Recrystallization from water-methanol, followed by drying under reduced pressure at 50° C., yielded 6.5 g of colorless crystals of disodium(3-carboxylato-7-ethyl-5-oxo-5H-[1]benzopyrano[2,3-b]pyridin-2-yl)acetate. m.p. 275°–280° C. (decomp.).

By the similar procedure as described above, there were obtained the following compounds:

From methyl(3-methoxycarbonyl-7-isopropyl-5-oxo-5H-[1]benzopyrano[2,3-b]pyridin-2-yl)acetate, disodium(3-carboxylato-7-isopropyl-5-oxo-5H-[1]benzopyrano[2,3-b]pyridin-2-yl)acetate as colorless crystals (water-methanol) (which did not show the definite melting point).

Infra-red absorption spectrum (KBr)cm$^{-1}$: 1660, 1580

Nuclear magnetic resonance spectrum ($D_2O$)δ: 8.43(1H,s), 7.36(1H,s like), 7.28(1H,dd,J=2 and 8 Hz), 6.89(1H,d,J=8 Hz), 4.33(2H,s), 2.66(1H,quintet,J≈6 Hz), 1.20(6H,d,J=6.5 Hz).

From methyl(3-methoxycarbonyl-11-n-propyl-7,8,9,10-tetrahydro-5-oxo-5H-naphtho[2′,3′-2,3]pyrano[6,5-b]pyridin-2-yl)acetate, disodium(3-carboxylato-11-n-propyl-7,8,9,10-tetrahydro-5H-naphtho[2′,3′-2,3]pyrano[6,5-b]pyridin-2-yl)acetate as colorless needles (water-methanol).

Infra-red absorption spectrum (KBr) cm$^{-1}$: 3400, 1670, 1650, 1630, 1605, 1575.

Nuclear magnetic resonance spectrum ($D_2O$)δ: 8.51(1H,s), 6.95(1H,s), 4.18(2H,s), ca 2.37(6H,m), 1.48(4H,m), ca 1.1(2H,m), 0.82(3H,t,J=6 Hz).

EXAMPLE 5

A mixture of methyl(3-methoxycarbonyl-5-oxo-5H-[1]benzopyrano[2,3-b]pyridin-2-yl)acetate (3.27 g), 80% sulfuric acid (20 ml) and acetic acid (4 ml) was heated at 70° C., and water (7 ml) was added to the mixture, followed by heating for 2.5 hours. Water was added to the reaction solution, and a precipitate was recovered by filtration, washed with chloroform and stirred together with 1N aqueous sodium hydroxide solution (40 ml) at room temperature for 4 hours. Methanol (60 ml) was added to the mixture, and the crystals which separated out were recovered by filtration and recrystallized from water-methanol to give 2.66 g of colorless long needles of disodium(3-carboxylato-5-oxo-5H-

[1]benzopyrano[2,3-b]-pyridin-2-yl)acetate (no definite melting point was observed).

Infra-red absorption spectrum (KBr) cm$^{-1}$: 3400, 1650–1600.

Nuclear magnetic resonance spectrum (D$_2$O)δ: 8.33(1H,s), 6.89–7.67(4H,m), 4.09(2H,s).

Elemental analysis, for C$_{15}$H$_7$NO$_6$Na$_2$.2H$_2$O: Calcd. (%): C, 47.50; H, 2.92; N, 3.69; Found (%): C, 47.49; H, 2.71; N, 3.95

By following the similar procedure, there were obtained the compounds as described below:

From methyl(7-chlor-3-methoxycarbonyl-5-oxo-5H-[1]benzopyrano[2,3-b]pyridin-2-yl)acetate, disodium(7-chlor-3-carboxylato-5-oxo-5H-[1]benzopyrano[2,3-b]pyridin-2-yl)acetate as colorless needles (water-methanol).

Infra-red absorption spectrum (KBr) cm$^{-1}$: 1665, 1600

Nuclear magnetic resonance spectrum (D$_2$O)δ: 8.42(1H,s), 7.36(1H d,J=2 Hz), 7.30(1H,dd,J=2 and 9 Hz), 7.02(1H,d,J=9 Hz), 4.13(2H,s).

From methyl(7,9-dimethyl-3-methoxycarbonyl-5-oxo-5H-[1]benzopyrano[2,3-b]pyridin-2-yl)acetate, disodium(3-carboxylato-7,9-dimethyl-5-oxo-5H-[1]benzopyrano[2,3-b]pyridin-2-yl)acetate as colorless needles (water-methanol).

Infra-red absorption spectrum (KBr) cm$^{-1}$: 3400, 1670, 1630–1580

Nuclear magnetic resonance absorption (D$_2$O)δ: 8.25(1H,s), 6.67(1H,br.s), 6.48(1H,br.s), 4.12(2H,s), 1.90(3H,s), 1.82(3H,s).

From methyl(3-methoxycarbonyl-5-oxo-5H-[1]naphtho[2',1'-2,3]pyrano[6,5-b]pyridin-2-yl)acetate, disodium(3-carboxylato-5-oxo-5H-[1]naphtho[2',1'-2,3]pyrano[6,5-b]pyridin-2-yl)acetate as colorless needles (water-methanol).

Infra-red absorption spectrum (KBr) cm$^{-1}$: 3400, 1650, 1615, 1578, 1385

Nuclear magnetic resonance spectrum (D$_2$O)δ: 8.60(1H,m), 7.97(1H,s), 7.38(1H,d,J=9 Hz), ca 7.05(3H,m), 6.70(1H,d, J=9 Hz) 4.05(2H,s).

From methyl(7-methoxy-3-methoxycarbonyl-5-oxo-5H-[1]benzopyrano[2,3-b]pyridin-2-yl)acetate, disodium(3-carboxylato-7-methoxy-5-oxo-5H-[1]benzopyrano[2,3-b]pyridin-2-yl)acetate as colorless needles (water-methanol). m.p. 190°–200° C. (decomp.).

Infra-red absorption spectrum (KBr) cm$^{-1}$: 3650–2900, 1645, 1620, 1610, 1585, 1545.

Nuclear magnetic resonance spectrum (D$_2$O)δ: 8.77(1H,s), 7.1–7.5(3H,m), 4.38(2H,s), 3.89(3H,s).

EXAMPLE 6

A mixture of ethyl 3-(3-ethoxycarbonyl-7-ethyl-5-oxo-5H-[1]benzopyrano[2,3-b]pyridin-2-yl)propionate (2.6 g), 80% sulfuric acid (16 ml) and acetic acid (4 ml) was heated at 70° C. to dissolve, and subsequently, water (8 ml) was added to the solution over a 20-minute period, followed by raising the temperature to 100° C. After heating at 100° C. for 2 hours, water was added to the reaction solution, and a precipitate was recovered by filtration and washed with water. The resultant white solid was dissolved in 1N aqueous sodium hydroxide solution (45 ml), and the solution was stirred at room temperature. 1.5 Hours later, concentrated sulfuric acid was added to acidify the reaction solution, and the solid which separated out was recovered by filtration. Recrystallization from dimethylformamide-water yielded 2.01 g of colorless fine crystals of 3-(3-carboxy-7-ethyl-5-oxo-5H-[1]benzopyrano[2,3-b]pyridin-2-yl)propionic acid. m.p. 284°–287° C. (decomp.).

By following the similar procedure, from ethyl 3-(7-chlor-3-ethoxycarbonyl-5-oxo-5H-[1]benzopyrano[2,3-b]pyridin-2-yl)propionate was prepared 3-(3-carboxy-7-chlor-5-oxo-5H-[1]benzopyrano[2,3-b]pyridin-2-yl)propionic acid as colorless needles (dimethylformamide). m.p. 295°–298° C. (decomp. under foaming).

EXAMPLE 7

A mixture of 6-ethyl-4-oxo-4H-1-benzopyran-3-carbonitrile (8.00 g), diethyl 1,3-acetonedicarboxylate (8.8 g) ethanol (70 ml) and piperidine (0.5 ml) was heated under reflux for 2 hours. After the reaction mixture was cooled, the crystals which separated out were recovered by filtration and washed with ethanol to give 12 g of pale yellow crystals. 1.5 g of the obtained crystals were weighed out, chromatographed on a column of silica gel (100 g), and eluted with hexane-chloroform-acetone-formic acid (20:20:1:0.05) to conduct the purification. Recrystallization from ethanol produced 1.3 g of colorless needles of ethyl(7-ethyl-3-ethoxycarbonyl-5-oxo-5H-[1]benzopyrano[2,3-b]pyridin-2-yl)acetate. m.p. 123°–124° C.

EXAMPLE 8

6-Chlor-4-oxo-4H-1-benzopyran-3-carbonitrile (5 g), piperidine (0.56 ml) and diethyl 1,3-acetonedicarboxylate (4.6 ml) were added to ethanol (50 ml) and the mixture was heated under reflux for 1.5 hours. The crystals which separated out were recovered by filtration and washed with ether until no more washing is colored. Recrystallization from chloroform-ethanol produced 6.17 g of pale yellow needles of ethyl(7-chlor-3-ethoxycarbonyl-5-oxo-5H-[1]benzopyrano[2,3-b]pyridin-2-yl)acetate. m.p. 148°–149° C.

| Example of preparations (tablet). | |
|---|---|
| Disodium (3-carboxylato-7-ethyl-5-oxo-5H—[1]benzopyrano[2,3-b]pyridin-2-yl)acetate: | 50 mg |
| Lactose: | 150 mg |
| Corn starch: | 35 mg |
| Microcrystallinic cellulose: | 30 mg |
| Magnesium stearate: | 5 mg |
| | 270 mg per tablet |

The above ingredients were stirred and mixed to a uniform mixture, and compressed to a tablet in accordance with a conventional method.

What we claim is:

1. A compound of the formula:

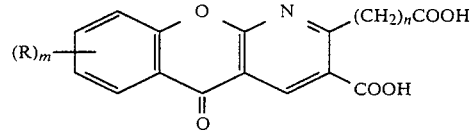

wherein R is the same or different and represents hydrogen, C$^{1-6}$-alkyl, C$^{1-4}$-alkoxy, nitro, hydroxyl, C$^{1-3}$-alkyl-CO, C$^{1-4}$-hydroxyalkyl or halogen where m is 1,2 or 3, or a —(CH$_2$)$_4$— or —CH=CH—CH=CH— group which, in conjunction with two adjacent carbon atoms on the ring, forms a six-membered ring where m is 1; and wherein n is 1 or 2, or a physiologically acceptable salt or ester thereof.

2. A process for producing a compound of the formula:

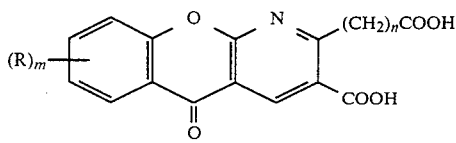

where R is the same or different and represents hydrogen, $C^{1-6}$-alkyl, $C^{1-4}$-alkoxy, nitro, hydroxyl, $C^{1-3}$-alkyl-CO, $C^{1-4}$-hydroxyalkyl or halogen where m is 1,2 or 3, or a —$(CH_2)_4$— or —CH═CH—CH═CH— group which, in conjunction with two adjacent carbon atoms on the ring, forms a six-membered ring where m is 1; and wherein n is 1 or 2, or a physiologically acceptable salt or ester thereof, which comprises reacting a compound of the formula:

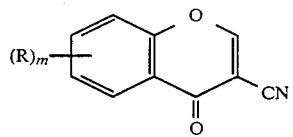

wherein R and m have the same meaning as defined above, with a compound of the formula:

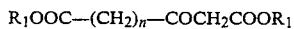

R₁OOC—(CH₂)ₙ—COCH₂COOR₁ wherein $R_1$ is alkyl and n has the same meaning as defined above, followed by subjecting the resultant reaction product to a hydrolysis reaction, if necessary.

3. A pharmaceutical composition for the treatment of connective tissue and inflammatory diseases which contains an amount effective for such treatment of a compound of the formula:

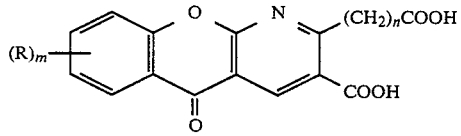

wherein R is the same or different and represents hydrogen, $C^{1-6}$-alkyl, $C^{1-4}$-alkoxy, nitro, hydroxyl, $C^{1-3}$-alkyl CO, $C^{1-4}$-hydroxyalkyl or halogen where m is 1, 2 or 3, or a —$(CH_2)_4$— or —CH═CH—CH═CH— group which, in conjunction with two adjacent carbon atoms on the ring, forms a six-membered ring where m is 1; and wherein n is 1 or 2, or a physiologically acceptable salt or ester thereof and a pharmaceutically acceptable carrier.

4. A compound as claimed in claim 1, wherein m is 1.
5. A compound as claimed in claim 1, wherein m is 2.
6. A compound as claimed in claim 1, wherein n is 1.

7. A compound as claimed in claim 1, wherein R is $C^{1-6}$-alkyl.
8. A compound as claimed in claim 1, wherein R is $C^{1-4}$-hydroxyalkyl.
9. A compound as claimed in claim 1, wherein R is halogen.
10. A compound as claimed in claim 1, wherein R is $C^{1-6}$-alkyl, m is 1 and n is 1.
11. A compound as claimed in claim 1, wherein R is $C^{1-4}$-hydroxyalkyl, m is 1 and n is 1.
12. A compound as claimed in claim 1, wherein R is halogen, m is 1 and n is 1.
13. A compound as claimed in claim 1, wherein the compound is methyl(7-ethyl-3-methoxycarbonyl-5-oxo-5H-[1]benzopyrano[2,3-b]pyridin-2-yl)acetate.
14. A compound as claimed in claim 1, wherein the compound is ethyl(7-ethy-3-ethoxycarbonyl-5-oxo-5H-[1]benzopyrano[2,3-b]pyridin-2-yl)acetate.
15. A compound as claimed in claim 1, wherein the compound is disodium(7-ethyl-3-carboxylato-5-oxo-5H-[1]benzopyrano[2,3-b]pyridin-2-yl)acetate.
16. A compound as claimed in claim 1, wherein the compound is methyl(3-methoxycarbonyl-5-oxo-5H-[1]benzopyrano[2,3-b]pyridin-2-yl)acetate.
17. A compound as claimed in claim 1, wherein the compound is methyl(7-chlor-3-methoxycarbonyl-5-oxo-5H-[1]benzopyrano[2,3-b]pyridin-2-yl)acetate.
18. A compound as claimed in claim 1, wherein the compound is ethyl(7-chlor-3-ethoxycarbonyl-5-oxo-5H-[1]benzopyrano[2,3-b]pyridin-2-yl)acetate.
19. A compound as claimed in claim 1, wherein the compound is disodium(7-chlor-3-carboxylato-5-oxo-5H-[1]benzopyrano[2,3-b]pyridin-2-yl)acetate.
20. A compound as claimed in claim 1, wherein the compound is methyl(7-isopropyl-3-methoxycarbonyl-5-oxo-5H-[1]benzopyrano[2,3-b]pyridin-2-yl)acetate.
21. A compound as claimed in claim 1, wherein the compound is methyl(7,9-dimethyl-3-methoxycarbonyl-5-oxo-5H-[1]benzopyrano[2,3-b]pyridin-2-yl)acetate.
22. A compound as claimed in claim 1, wherein the compound is ethyl(7-nitro-3-ethoxycarbonyl-5-oxo-5H-[1]benzopyrano[2,3-b]pyridin-2-yl)acetate.
23. A compound as claimed in claim 1, wherein the compound is ethyl(7-(1-hydroxyethyl)-3-ethoxycarbonyl-5-oxo-5H-[1]benzopyrano[2,3-b]pyridin-2-yl)acetate.
24. A compound as claimed in claim 1, wherein the compound is methyl(7-t-butyl-3-methoxycarbonyl-5-oxo-5H-[1]benzopyrano[2,3-b]pyridin-2-yl)acetate.
25. A compound as claimed in claim 1, wherein the compound is methyl(7-methoxy-3-methoxycarbonyl-5-oxo-5H-[1]benzopyrano[2,3-b]pyridin-2-yl)acetate.
26. A compound as claimed in claim 1, wherein the compound is methyl(7-hydroxy-3-methoxycarbonyl-5-oxo-5H-[1]benzopyrano[2,3-b]pyridin-2-yl)acetate.
27. A compound as claimed in claim 1, wherein the compound is ethyl(7-acetyl-3-ethoxycarbonyl-5-oxo-5H-[1]benzopyrano[2,3-b]pyridin-2-yl)acetate.

* * * * *